United States Patent [19]

Henneke et al.

[11] Patent Number: 4,650,910

[45] Date of Patent: Mar. 17, 1987

[54] PROCESS FOR THE PREPARATION OF SUBSTITUTED STYRENES

[75] Inventors: Karl-Wilhelm Henneke, Leverkusen; Karlfried Wedemeyer, Cologne, both of Fed. Rep. of Germany

[73] Assignee: Bayer Aktiengesellschaft, Leverkusen, Fed. Rep. of Germany

[21] Appl. No.: 836,037

[22] Filed: Mar. 4, 1986

[30] Foreign Application Priority Data

Mar. 6, 1985 [DE] Fed. Rep. of Germany ....... 3507824

[51] Int. Cl.$^4$ ...................... C07C 25/24; C07C 25/28; C07C 21/24; C07C 43/225
[52] U.S. Cl. .................................. 568/655; 568/648; 568/649; 568/656; 568/658; 570/193; 570/200; 585/435
[58] Field of Search ............... 568/648, 649, 656, 658, 568/655; 570/200, 193; 585/435

[56] References Cited

PUBLICATIONS

Jour. Chem. Soc. (1949) 1074.
Tetrahedron Letter, No. 5, 1968, Seiten 613–616, Pergamon Press, Oxfor, GB; A. Novelli et al.: "A new synthesis of trans-stilbenes".

*Primary Examiner*—Bernard Helfin
*Attorney, Agent, or Firm*—Sprung Horn Kramer & Woods

[57] ABSTRACT

Substituted styrenes are prepared by treatment on N-acyl-B-phenethylamines with bases and removal by distillation of the styrene which is formed during the reaction.

7 Claims, No Drawings

PROCESS FOR THE PREPARATION OF SUBSTITUTED STYRENES

The present invention relates to a process for the preparation of substituted styrenes from substituted N-acyl-β-phenethylamines.

Because of the great importance of substituted styrenes in preparative and industrial chemistry, there are numerous methods for their preparation. However, those processes which exist for the specific preparation of pure, isomer-free, substituted styrenes are frequently not optimum from the economic viewpoint.

Thus, it is known that styrenes can be prepared from ethylbenzenes by catalytic dehydrogenation (DE-OS (German Published Specification) No. 2,317,525). The disadvantage of this process is that reaction of the starting material is usually incomplete and thus, elaborate distillation is needed. Furthermore, substituted ethylbenzenes, such as o-chloroethylbenzene, are not readily available on the industrial scale. The dehydrogenations can, furthermore, only be carried out in special apparatus.

The preparation of substituted styrenes in a two-stage reaction starting from substituted benzaldehydes is known. After reaction with Grignard reagents, β-hydroxyalkylbenzenes are obtained and can be dehydrated by acid [U.S. Patent Specification No. 2,404,319; Org. Syn., Coll. Vol. III, 204 (1955)]. The disadvantages of this process are the great industrial elaboration necessary for carrying out the Grignard reactions, the unsatisfactory yield, and the frequently high price of the starting aldehydes high. If aldehydes are subjected to a Perkin reaction with acetic anhydride, and the resulting cinnamic acids decarboxylated, substituted styrenes are usually produced only in unsatisfactory yields [Ind. Eng. Chem. 50, 1005 (1958); Org. Syn., Coll. Vol. IV, 731 (1963)].

It is also known that styrenes can be prepared from substituted toluenes using methyl halides above 700° C. (U.S. Pat. Specification No. 3,636,182). The disadvantages of this process, which can be carried out only in special apparatus, are the incomplete conversion, the low selectivity and the great elaboration of the preparation of the pure substances.

It is also possible to prepare substituted styrenes from benzyl chlorides by a Wittig reaction in two stages using triphenylphosphine and formaldehyde (see Houben-Weyl, Vol. 5/1b, pages 383 et seq.) The disadvantages of this process are the need to use equimolar amounts of a costly auxiliary reagent and the disposal of large amounts of triphenylphosphine oxide, which limits the economics of the process.

Some N-acetyl-β-aminoalkylbenzenes in boiling xylene, in the presence of phosphorus pentoxide, eliminate acetamide and provide, for example, the central double-bond in stilbenes. The disadvantages of these syntheses are the use of at least molar amounts of phosphorus pentoxide and the unsatisfactory yields (J. Chem. Soc. 1949, 1074). Central double-bonds in stilbenes can also be prepared by elimination of acetamide in the presence of hydrochloric acid (Tetrahedron Letters 1968, 613). However, it is probable that this method remains restricted to the preparation of specially activated stilbenes.

It is also known to prepare α-alkylstyrenes from α-functionalized alkylbenzenes (European Patent No. 110,536). The disadvantage of this method is that the elimination of, for example, water from α-hydroxyalkylbenzenes does not take place uniformly. It entails the production of both styrenes with a terminal double-bond in the alkyl chain and of styrenes with the double-bond in the 2-position in the alkyl chain.

A process for the preparation of substituted styrenes of the general formula

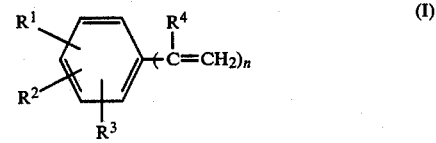

has now been found, in which
R$^1$ to R$^3$ are identical or different and represent hydrogen, halogen, lower alkyl or lower alkoxy each of which is optionally substituted by halogen,
R$^4$ denotes hydrogen or lower alkyl, and
n represents 1 or 2,
which process is characterized in that N-acyl-β-phenethylamines of the general formula

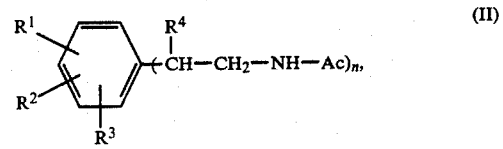

in which
Ac represents an acyl radical of an aliphatic or aromatic carboxylic acid, and
R$^1$ to R$^4$ and n have the abovementioned meaning, are treated with bases and the styrene which is formed is removed by distillation during the reaction.

Suitable lower alkyl radicals are those having 1 to 5, preferably 1 to 4, carbon atoms, such as the methyl, ethyl, n-propyl, iso-propyl, n-butyl, iso-butyl, sec.-butyl and tert.-butyl radical, particularly preferably the methyl, ethyl and iso-propyl radical; suitable lower alkoxy radicals are those having 1 to 5, preferably 1 to 3, carbon atoms, such as the methoxy, ethoxy, propoxy and isopropoxy radical. Examples of halogen-substituted alkyl or alkoxy groups which may be mentioned are: the trifluoromethyl and trifluoromethoxy group.

Halogens which may be mentioned are: fluorine, chlorine, bromine and iodine, preferably fluorine and chlorine.

It is possible to prepare by the process according to the invention, for example: 2-chlorostyrene, 3-chlorostyrene, 4-chlorostyrene, 3,4-dichlorostyrene, 2,4-dichlorostyrene, α-methyl-3-chlorostyrene, α-ethyl-3-chlorostyrene, α-isopropyl-3-chlorostyrene, α-butyl-3-chlorostyrene, α-methyl-4-chlorostyrene, α-ethyl-4-chlorostyrene, α-isopropyl-4-chlorostyrene, α-butyl-4-chlorostyrene, α-methyl-3,4-dichlorostyrene, α-ethyl-3,4-dichlorostyrene, α-isopropyl-3,4-dichlorostyrene, α-butyl-3,4-dichlorostyrene, 2,6-dichlorostyrene, 2-bromostyrene, 2,4-dibromostyrene, 3-bromostyrene, 4-bromostyrene, 2-fluorostyrene, 3-fluorostyrene, 4-fluorostyrene, α-methyl-4-fluorostyrene, α-methyl-4-fluorostyrene, α-isopropyl-4-fluorostyrene, α-n-butyl-4-fluorostyrene, 2-methylstyrene, 3-methylstyrene, 4-methylstyrene, 2-methoxystyrene, 4-methoxystyrene, 2-trifluoromethylstyrene, 3-trifluoromethylstyrene, 4- trifluoromethoxystyrene, p-divinylbenzene, m-divinylbenzene and o-divinylbenzene.

The acyl radical in the starting material (see formula (II)) is derived from carboxylic acids or carboxylic acid derivatives which are readily available at low cost as acylating agents for amines; thus, for example, the acetyl, proprionyl, isobutyryl radical and the benzoyl radical. The N-acetyl-β-phenethylamines as emerge from the formula (II) are preferably used in the process according to the invention.

Suitable bases for the process according to the invention are all compounds which are able to convert, in chemical equilibrium, the N-acylamino group into the anion. These may be alcoholates, such as sodium methylate, sodium ethylate, sodium isobutylate and/or potassium tert.-butylate, preferably sodium methylate and/or potassium tert.-butylate.

Also suitable are the alkali metal salts of primary and secondary amines, ammonia and alkali metal hydrides. Examples which may be mentioned are: sodium amide, lithium diisoproylamide and/or sodium hydride.

It is also possible to use the cyanides, carbonates and/or fluorides of the alkali metal and/or alkaline earth metals, such as sodium carbonate, potassium carbonate, sodium bicarbonate, potassium fluoride, sodium fluoride and/or calcium carbonate. In such cases it is advantageous, where appropriate, if phase-transfer catalysts which are able to increase the solubility of the salts in the organic phase are also added; in the case of the potassium ion, for example, crown ethers, such as 18-crown-6, or polyglycols.

The amount of the bases used in the process according to the invention can be varied within wide limits. In general, about 0.1 to 100 mol %, preferably 1 to 50 mol %, particularly preferably 2 to 10 mol %, relative to N-acyl-β-phenethylamine of the general formula (II), are used. The optimum amount can readily be determined by preliminary experiments.

In the process according to the invention the styrene which is formed is removed by distillation during the reaction.

In general, the reaction temperature depends on the constitution of the N-acyl-β-phenethylamine used. The temperature is usually about 150° to 250° C., preferably 160° to 200° C.

The addition of a solvent and/or diluent is, in principle, unnecessary and, in most cases, is also superfluous. When higher-melting starting materials are used it may, where appropriate, be advantageous to use solvents and/or diluents. Suitable inert solvents and/or diluents are aliphatic and/or aromatic hydrocarbons, aliphatic and/or aromatic ethers and halogenated aromatic hydrocarbons. Their boiling points can be sufficiently high for them to remain in the bottom under the distillation conditions. However, it is advantageous, where appropriate, to choose their boiling point such that the solvents and/or diluents also distil over, entirely or partially, under the reaction and distillation conditions. Styrenes which are prone to polymerize such as divinylbenzenes, are thus diluted and displaced more rapidly from the hotter parts of the apparatus. Examples of suitable solvents and/or diluents which may be mentioned are: phenanthrene, o/m-terphenyl, polyglycol ethers, polyglycols, phenoxydiphenyls and/or isomeric tolyl ethers.

When N-acetyl-2-(2-chlorophenyl)ethylamine and sodium methylate are used as starting materials in the process according to the invention, then the course of the reaction can be represented by the following equation:

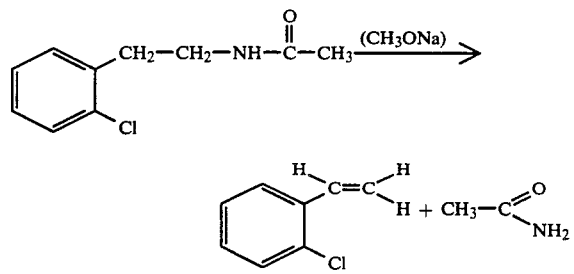

The process according to the invention can be carried out, for example, in a customary distillation apparatus, as follows. The apparatus consists of a reaction flask with a 10 to 20 cm Vigreux column attached and, on top of this, an air condenser which passes the products into a receiver which can be cooled. The N-acylphenethylamine of the formula (II), about 2 to 10 mol % of alcoholate and about 0.1% by weight of tert.-butylcatechol are initially introduced, and the same amount of stabiliser is placed in the distillation receiver. After a vacuum of 10 to 20 mbar has been applied, the temperature is raised to about 150° to 250° C. During this the cleavage products distil over. Acetamide usually crystallizes completely out of the distillate in the receiver. It can be separated from the styrene by filtration or by washing with water. After basic constituents, which may be present in small amounts, have been washed out with dilute hydrochloric acid, the styrenes are obtained in high purity by redistillation using a still head or a short column.

It is possible, where appropriate, to dispense with the addition of a polymerization stabiliser, especially in the case of styrenes of the general formula (I), in which $R^4$ is an alkyl group.

The process according to the invention can also be carried out continuously by a portion of the N-acetylβ-phenethylamine being initially introduced into a smaller apparatus and further starting material being metered in depending on the progress of the reaction and distillation.

The substituted N-acyl-β-phenethylamines used in the process according to the invention can easily be prepared in a manner known per se from the correspondingly substituted benzyl chlorides (see preparation examples). As is evident from the formula diagram, first a chloro/cyano exchange takes place. The benzyl cyanides can be alkylated in the α-position. Following hydrogenation to give the β-phenethylamines and subsequent acylation, the starting material of the general formula (II) is obtained.

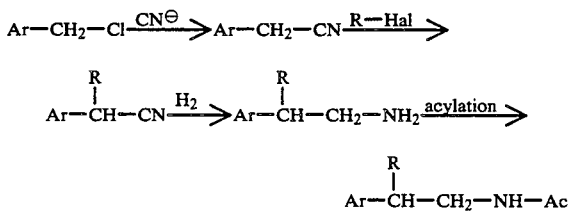

The process according to the invention has several advantages as compared with the state of the art. Pure, isomer-free styrenes can be prepared in high yield and quality, and in reaction steps in customary apparatus which are straightforward to carry out industrially, from readily available pure benzyl chlorides. Exclusively products with a terminal double-bond are produced from derivatives which are side-chain alkylated.

Substituted styrenes have a wide variety of uses in polymer and active compound chemistry. On copolymerization they are used to modify the properties of the products (see Ullmanns Encyclopädie der technischen Chemie [Encyclopaedia of Industrial Chemistry], 4th edition, volume 22, pages 306 et seq.). Recently, new active compounds based on substituted styrenes have been described and can be used as plant-protection agents.

The examples which follow are intended to illustrate the process according to the invention.

EXAMPLE 1

A vacuum distillation apparatus, consisting of a 500 ml three-neck flask with an internal thermometer, 10 cm Vigreux column and attached still head and receiver, is flushed with nitrogen. 197.5 g (1 mol) of N-acetyl-2-(2-chlorophenyl)ethylamine, 5.9 g (50 mmol) of potassium tert.-butylate (95% pure) and 0.2 g of tert.-butylcatechol are placed in the flask, and 0.2 g of the same stabiliser is placed in the receiver. After a pressure of 20 mbar has been set up, the starting material is heated. The reaction starts at a bottom temperature of about 160° C. and is detectable by the appearance of cleavage products in the condenser. The reaction is completed within 1 to 2 h by heating up to a bottom temperature of 200° C. The vacuum is finally increased to about 5 mbar for a short time. 188.3 g of distillate are obtained, and the acetamide substantially crystallizes out of this. The distillate is taken up in 300 ml of ether and 200 ml of water, the aqueous phase is separated off, and the organic phase is washed successively with 5% strength hydrochloric acid and aqueous sodium bicarbonate solution. After drying and removal of the solvent by distillation, 133.3 g of residue which contains 99.1% of o-chlorostyrene are obtained. Yield 95.4% of theory.

EXAMPLES 2 to 7

The process is carried out as described in Example 1, but the bases indicated in the Table are used. The distillation bottoms were heated up to 220° C.

| Example | Base | Mol-%[1] | Yield % of theory | Selectivity[2] % |
|---|---|---|---|---|
| 2 | Sodium methylate | 4 | 94 | 95 |
| 3 | Potassium isobutylate | 5 | 94 | 95 |
| 4 | NaCN | 10 | 32 | 84 |
| 5 | KCN[3] | 5 | 90 | 95 |
| 6 | K$_2$CO$_3$[3] | 2.5 | 86 | 92 |
| 7 | KF[3] | 5 | 45 | 78 |

[1]based on N—acetyl-2-(2-chlorophenyl)ethylamine
[2]based on reacted starting material
[3]18-crown-6 also added, amount equivalent to potassium ions.

EXAMPLES 8 to 25

The process is carried out as described in Example 1, and the substituted styrenes in the Table are obtained from the corresponding N-acetyl precursors of the general formula (II).

| Example | R$^1$ | R$^2$ | K—tert.-[1] butylate mol % | Cleavage[2] temperature °C. | Distillation pressure, mbar | Styrene[3] yield % of theory | Selectivity[4] % |
|---|---|---|---|---|---|---|---|
| 8 | 4-Cl | H | 5 | 170–185 | 20 | 91 | 92 |
| 9 | 2,4-Cl$_2$ | H | 10 | 160–180 | 10 | 73 | 91 |
| 10 | 3,4-Cl$_2$ | H | 10 | 160–180 | 10 | 85 | 89 |
| 11 | 4-Cl | (CH$_3$)$_2$CH | 10 | 180–190 | 10 | 62 | 86 |
| 12 | 4-Cl | (CH$_3$)$_2$CH | 10[5] | 180–190 | 10 | 82 | 92 |
| 13 | 4-Cl | CH$_3$—CH$_2$ | 25 | 180–190 | 10 | 83 | 93 |
| 14 | 3,4-Cl$_2$ | (CH$_3$)$_2$CH | 25 | 170–195 | 10 | 80 | 89 |
| 15 | 4-CH$_3$ | H | 40 | 185–200 | 20 | 64 | 81 |
| 16 | 4-CH$_3$ | H | 10[5] | 180–205 | 20 | 81 | 95 |
| 17 | 4-F | H | 10 | 170–190 | 20 | 85 | 89 |
| 18 | 2-F | H | 20 | 170–200 | 20 | 40 | 67 |
| 19 | 4-Br | H | 5 | 180–205 | 10 | 29 | 88 |
| 20 | 4-Br | H | 10[5] | 175–210 | 10 | 73 | 91 |
| 21 | 2-Br | H | 10[5] | 180–190 | 10 | 87 | 88 |
| 22 | 3-CF$_3$ | H | 20 | 165–200 | 20 | 80 | 84 |
| 23 | 2-CF$_3$ | H | 30 | 165–180 | 20 | 50 | 72 |
| 24 | 4-CF$_3$O | H | 20 | 175–200 | 10 | 64 | 80 |
| 25 | 4-CH$_3$O | H | 40 | 190–250 | 10 | 45 | 47 |

[1]based on acetylphenethylamine of the formula (II)
[2]guidelines
[3]in the distillate
[4]styrene yield based on reacted acetylphenylethylamine. Part of the unreacted starting material is in the distillate and part is in the distillation residue.
[5]18-crown-6 also added. Amount equimolar to the amount of base.

EXAMPLE 26

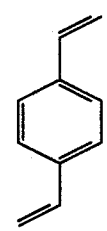

Under N₂, 248.3 g (1 mol) of 1,4-bis(2-acetaminoe-thyl)benzene, 11.2 g (100 mmol) of potassium tert.-butylate, 95% pure, 26.4 g (100 mmol) of 1,4,7,10,13,16-hexaoxacyclooctadecane (18-crown-6), 250 g of a mixture of isomeric phenoxydiphenyl ethers, 250 mg of tert.-butylcatechol and 250 mg of p-phenylenediamine are initially introduced into a distillation apparatus analogous to Example 1. An additional 250 mg of tert.-butylcatechol are placed in the distillation receiver. After a vacuum of 10 mbar has been applied, the temperature of the bottom is increased. The cleavage reaction starts at about 175° C. and is detectable by the appearance of the products in the still head. The reaction is completed in 1–2 h by slowly increasing the bottom temperature to 210° C. Finally, the vacuum is increased to 5 mbar for a short time. The distillate is taken up in 300 ml of ether and 200 ml of water, the aqueous phase is separated off, and the organic phase is washed once more with 200 ml of water, dried with sodium sulfate and the solvent is removed by distillation in vacuo. 213.2 g of residue contains 58.4% of p-divinylbenzene (96% of theory), 2.6% of 4-(2-acetaminoethyl)styrene and 37.3% of isomeric phenoxydiphenyl ethers. 111.0 g of p-divinylbenzene are obtained with a boiling point of 40°–41° C. at about 0.5 mbar after renewed distillation over a 20 cm Vigreux column. Yield 85% of theory. Purity 99.9%.

EXAMPLE 27

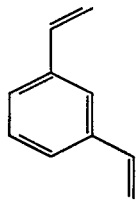

248.3 g (1 mol) of 1,3-bis(2-acetaminoethyl)benzene are used and the process is carried out as described in Example 26. 191.8 g of ether residue contain 58.2% of m-divinylbenzene (86% of theory), 10.0% of 3-(2-acetaminoethyl)styrene and 30.1% of isomeric phenoxydiphenyl ethers. 104.5 g of m-divinylbenzene are obtained after distillation over a 20 cm Vigreux column. Yield 80% of theory, purity 99.6%.

EXAMPLE 28

The process is initially carried out as described in Example 1. When the cleavage products distil over another mol of N-acetyl-2-(2-chlorophenyl)ethylamine is added dropwise, from a dropping funnel, to the reaction flask. The rate of addition is adjusted so that the amount added dropwise approximately corresponds to the amount of the distillate. The amount of base is 2.5 mol % relative to the total of acetyl compound employed.

After working up, 274.4 g of ether residue are obtained, which contains 97.2%=266.6 g=96% of theory of o-chlorostyrene.

EXAMPLE 29

259.7 g (1 mol) of n-benzoyl-2-(2-chlorophenyl)ethylamine are used and the process is otherwise carried out as in Example 1. At a bottom temperature of up to 200° C. and a top temperature of 140° C. under 20 mbar, 73.6 g of distillate which contains 82.6%=60.8 g=44% of theory of o-chlorostyrene are obtained. 188 g of distillation residue contain 134.2 g of starting compound. Selectivity 91%.

EXAMPLE 30

The process is carried out as described in Example 1, but potassium tert.-butylate is replaced by 5 g of powdered potassium carbonate and 100 g of polyglycol P 400. The bottom is heated up to 215° C. and the distillate is collected up to 140°C./6 mbar. 120.2 g of ether residue after working up contain 96.9% of o-chlorostyrene. Yield 84% of theory.

PREPARATION OF THE STARTING MATERIAL

(a) 4-Chloro/cyano exchange

4-Chlorobenzyl chloride 196 g (4 mol) of sodium Cyanide, 12.5 g (40 mmol) of tributylbenzylammonium chloride and 660 mL of water are initially introduced into a 2 l multineck apparatus with reflux condenser, internal thermometer and dropping funnel, and the mixture is heated to 90° C. At the same temperature, 644 g (4 mol) of molten 4-chlorobenzyl chloride are added dropwise in 1 h, and the mixture is then stirred for 2 h. After having been cooled to about 35° C., the organic phase is separated off, washed with water and fractionated over a short column. 552 g of 4-chlorobenzyl cyanide (91% of theory) are obtained.

(b) Side-chain alkylation

4-Chloro-α-isopropylbenzyl cyanide 469 g (3.1 mol) of 4-chlorobenzyl cyanide, 30 g of tetrabutylammonium bromide, 1500 g of 50% strength sodium hydroxide solution and 438 g (3.56 mol) of isopropyl bromide are initially introduced into a 4 l multineck apparatus with reflux condenser and internal thermometer. The temperature rises after the stirrer is switched on. It is maintained at 40° C. for 4 h, initially by cooling and later by heating. The reaction mixture is cooled to room temperature, poured into a mixture of 500 ml of ether and 500 ml of water, the aqueous phase is separated off, and the organic phase is washed successively with 5% strength hydrochloric acid, sodium bicarbonate solution and water. After having been dried with sodium sufate, the solvent is removed by distillation. The residue remaining is 585.3 g of 97% pure 4-α-isopropylbenzyl cyanide. The product is pure enough for the subsequent hydrogenation.

(c) Hydrogenation

4-Chloro-α-isopropyl-β-phenethylamine

A 0.7 l autoclave is charged with 400 g (2 mol) of 97% pure 4-chloro- -isopropylbenzyl cyanide, 23 g of Raney cobalt which is moist with methanol, and 80 g of ammonia (4.7 mol). The overall pressure is increased to 100 bar with hydrogen, and the mixture is heated at 130° C. The reaction is complete in about 1 h by subsequent injection of hydrogen to 100 to 150 bar. After cooling to room temperature, removal of the catalyst by filtration with suction and washing with methanol, the crude product is fractionally distilled through a column. 352 g (89% of theory) of 4-chloro-α-isopropyl-β-phenethylamine are obtained with a boiling point of 134°–135° C./16 mbar. Purity 99.8%

(d) Acetylation 395.4 g (2 mol) of 4-chloro-α-isopropyl-β-phenethylamine are added dropwise, with exclusion of moisture, in 1 h to 208 g (2.04 mol) of acetic anhydride, which has been initially introduced, at 60° C. The reaction mixture is then stirred at 60° C. for 2 h and distilled, while increasing the vacuum, through a still head. After removal of the acetic acid and the excess acetic anhydride, 460 g of pure N-acetyl-4-chloro-α-isopropyl-β-phenethylamine distil under oil pump vacuum at a boiling point of 168°–171° C. about 1–2 mbar.

All the other N-acetyl-β-phenethylamines of the general formula (II) were prepared by an analogous sequence of reactions. Where the starting material or products were solid, solvents were used, such as toluene for the chloro/cyano exchange and the side-chain alkylation, methanol for the hydrogenation, and acetic acid for the acetylation.

What is claimed is:

1. A process for the preparation of a substituted styrene of the formula

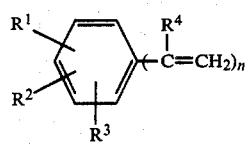

in which
$R^1$ to $R^3$ are identical or different and represent hydrogen, halogen, lower alkyl, lower alkoxy, lower alkyl substituted by halogen or lower alkoxy substituted by halogen,
$R^4$ denotes hydrogen or lower alkyl, and
n represents 1 or 2,
wherein an N-acyl-B-phenethylamine of the formula

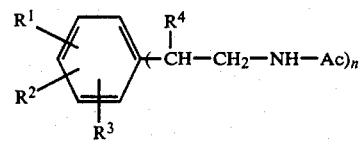

in which
Ac represents an acyl radical of an aliphatic or aromatic carboxylic acid, and
$R^1$ to $R^4$ and n have the abovementioned meaning,
is treated with a base and the styrene which is formed is removed by distillation during the reaction.

2. A process according to claim 1, wherein an N-acetyl-B-phenethylamine is used.

3. A process according to claim 1, wherein the base used is an alcoholate, an alkali metal salt of a primary or secondary amine, ammonia, an alkali metal hydride and/or cyanide, carbonate and/or fluoride of an alkali metal and/or alkaline earth metal.

4. A process according to claim 1, wherein a phase-transfer catalyst is added when a base which contains alkali metal and/or alkaline earth metal ion is used.

5. A process according to claim 1, wherein a crown ether or polyglycol is added as the phase-transfer catalyst.

6. A process according to claim 1, wherein the base is used in an amount of from 0.1 to 100 mol % relative to N-acyl-B-phenethylamine.

7. A process according to claim 1, wherein the base treatment is carried out at a temperature from 150° to 250° C.